(12) United States Patent
MacDougall et al.

(10) Patent No.: US 11,925,814 B2
(45) Date of Patent: Mar. 12, 2024

(54) OPTICAL APPLICATOR FEATURE OPTIMIZER

(71) Applicant: LUMEDA INC., Rocky Hill, CT (US)

(72) Inventors: Trevor MacDougall, South Dartmouth, MA (US); Yi Yang, Storrs, CT (US)

(73) Assignee: LUMEDA Inc., Rocky Hill, CT (US)

( * ) Notice: Subject to any disclaimer, the term of this patent is extended or adjusted under 35 U.S.C. 154(b) by 0 days.

(21) Appl. No.: 17/310,776

(22) PCT Filed: Mar. 19, 2021

(86) PCT No.: PCT/US2021/023176
§ 371 (c)(1),
(2) Date: Aug. 24, 2021

(87) PCT Pub. No.: WO2021/194877
PCT Pub. Date: Sep. 30, 2021

(65) Prior Publication Data
US 2023/0123262 A1    Apr. 20, 2023

Related U.S. Application Data

(60) Provisional application No. 62/994,404, filed on Mar. 25, 2020.

(51) Int. Cl.
*A61N 5/06* (2006.01)

(52) U.S. Cl.
CPC ...... *A61N 5/062* (2013.01); *A61N 2005/0626* (2013.01); *A61N 2005/0652* (2013.01)

(58) Field of Classification Search
CPC ...... A61B 18/20–18/28; A61N 5/06–2005/073
USPC .................................. 606/2–19; 607/88–94
See application file for complete search history.

(56) References Cited

U.S. PATENT DOCUMENTS

| | | | |
|---|---|---|---|
| 2003/0153825 A1* | 8/2003 | Mooradian | A61B 5/0059 600/407 |
| 2011/0037002 A1* | 2/2011 | Johnson | A61N 5/0613 250/493.1 |
| 2013/0115180 A1 | 5/2013 | Goren et al. | |
| 2017/0348542 A1 | 12/2017 | Betrouni et al. | |
| 2018/0207441 A1* | 7/2018 | Shafirstein | A61N 5/0616 |
| 2020/0046997 A1 | 2/2020 | Shafirstein et al. | |

* cited by examiner

*Primary Examiner* — Jonathan T Kuo
*Assistant Examiner* — Vynn V Huh
(74) *Attorney, Agent, or Firm* — Matthew J Patterson (57) ABSTRACT

A photodynamic therapy (PDT) apparatus and method are disclosed. The PDT apparatus includes a light flap that includes a plurality of light emitting devices wherein each of the light emitting devices has a plurality of operating states. The plurality of operating states are used to train a neural network model capable of producing a treatment irradiance profile. The method includes using an image of an area of interest for targeted treatment of PDT wherein the image is used an input to the trained neural network model. The neural network model produces a plurality of optimized feature states and the apparatus in turn produces a treatment irradiance profile closely matching the area of interest.

9 Claims, 8 Drawing Sheets

OPTICAL APPLICATOR FEATURE OPTIMIZER

CROSS REFERENCE TO RELATED APPLICATIONS

This application claims the benefit of U.S. Provisional Patent Application Ser. No. 62/994,404 filed 25 Mar. 2020 and is a as well as Patent Cooperation Treaty Patent Application Serial No PCT/US21/23176 filed 19 Mar. 2021. The disclosures of the applications above are incorporated herein by reference in their entirety.

BACKGROUND OF THE INVENTION

Field of the Invention

The present disclosure relates to non-ionizing photodynamic therapy.

Description of the Related Art

Light therapy can be used for treatment of conditions in multiple ways. For example, some light therapies involve the delivery of a therapeutic light through a fiber optic device placed proximal to or within a target tumor.

Some prior art light therapies can be combined with prior administration of light sensitive medicine (i.e., photosensitizer) that absorbs the therapeutic light and interacts with surrounding tissue constituents (e.g., oxygen) to generate reactive species that can destroy the target tissue. This form of therapy is known as photodynamic therapy ("PDT"). PDT uses light (such as light provided by a laser) to activate a non-toxic drug called a photosensitizer. The process works in three ways: it destroys cancer, shuts down blood vessels that "feed" the tumor, and prompts the immune system to kill cancer cells throughout the body. It is associated with mild side effects and can be combined with standard chemotherapy and surgery and followed with radiation therapy.

In addition, or alternatively, the energy of the light can be absorbed by blood or external additives (such as metal particles) that convert the light energy into heat, to induce complete destruction of the target tumor tissue.

In all light therapies, whether PDT or not, it can be important that the entire tumor be illuminated with sufficient dose light in order to administer a successful treatment. It is a deficiency in the prior art that it is difficult to know where and how much light is delivered to the tumor or tissue.

In addition, the efficacy of PDT is determined in part by photodynamic sensitizer availability and radiant exposure. Photofrin and other photodynamic sensitizers can be degraded by light exposure, a process called photobleaching, and this can be measured by loss of photosensitizer characteristic fluorescence. In addition, photobleaching has been shown to provide a prediction of the photodynamic dose delivered. However, quantitative measures of photosensitizer fluorescence can be complicated by changes in tissue optical properties during PDT.

An example of a prior art photodynamic light therapy delivery system and method is disclosed in US Patent Application No. 20180207442 wherein it is used for the treatment of a tissue. A plurality of light-transmitting catheters (LTCs) having diffusers mounted at a distal end are provided and placed in the tissue according to a pre-determined treatment plan, wherein an LTC includes a first treatment fiber disposed therethrough, and an LTC includes a dosimetry fiber disposed therethrough. A dose light is provided to the tissue via the light diffusers by way of the first treatment fiber according to the pre-determined treatment plan. The diffusers are manually positioned near the target tissue and the light is monitored using the dosimetry fiber. Light received at the dosimetry fiber is measured using a photodetector in operable communication with the dosimetry fiber. One or more properties of a photosensitizer in the tissue are determined. The treatment plan is modified based on the properties of the photosensitizer, and an updated dose light is provided to the tissue by way of the first treatment fiber according to the modified treatment plan.

Another example of prior art light therapy can be found in US Patent Application No. 20180207441 wherein a system and method are disclosed that use a flexible guide (flap) having optical fibers that emit light from a distal end and a scanning method to control the delivery of light dose to a treatment area. This approach overcomes the non-reliable delivery of light dose with a flap that conforms to the target area. Dosimetry control can be improved through the use of a computer controlled motor to move the laser fibers linearly within spheres at a known speed over the target tissue. The spheres position the distal ends of the optical fibers a known distance from the tissue. In some embodiments, treatment time is reduced and illumination of large surfaces is achieved by using multiple fibers to deliver the light simultaneously.

The examples of the prior art lack the ability to provide a known amount of light dosage to an entire surface of a tumor in a fast and efficient way. For at least the reasons stated herein before, it is desirable to provide light therapy device and method that alleviates the known problems.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for controlling an optical light delivery system. The method also includes providing a plurality of light emitting devices where each of the light emitting devices has a plurality of states and producing a plurality of irradiance profile arrays for each of the plurality of states of the plurality of light emitting devices and subdividing each of the plurality of irradiance profile arrays into a plurality of pixels, each pixel may include a portion of each of the plurality of irradiance profile arrays and determining a specific intensity level for each of the pixels. Other embodiments of this aspect include corresponding computer systems, apparatus, and computer programs recorded on one or more computer storage devices, each configured to perform the actions of the methods.

Implementations may include one or more of the following features. The method may include assigning a value to each of the pixels in accordance with the specific intensity level and generating a plurality of base cases representing the plurality of states of the plurality of light emitting devices. At least one training case is generated by performing at least one operation on at least one base case, the at least one operation selected from the group may include of performing a semi-random array modifier to the base case and performing geometric perturbations to the base case and normalizing a grayscale value of the base case and introducing a jitter into the base case. The method may include creating a neural network model and training the neural network model using at least the plurality of base cases and the plurality of training cases and producing a trained neural network. The method may include receiving tissue image data representing an organ and identifying an area of interest from the tissue image data and subdividing the area of interest into a plurality of tissue image pixels, each tissue image pixel may include a portion of the area of interest representing a respective portion of the organ and inputting the plurality of tissue image pixels into the trained neural network and determining a plurality of optimized feature states and outputting the plurality of optimized feature states. The method may include controlling the plurality of light emitting devices using the plurality of optimized feature states and producing a treatment irradiance profile closely matching at least a portion of the area of interest. The method may include positioning the plurality of light emitting devices proximate at least a portion of the area of interest and delivering the treatment irradiance profile to the area of interest. The treatment irradiance profile is delivered to the area of interest for a set period of time. The area of interest may include a tumor. The plurality of states is any of an off state, an on state, an intensity level and a wavelength. Implementations of the described techniques may include hardware, a method or process, or computer software on a computer-accessible medium.

One general aspect includes optical light delivery system that includes an opto-electronic instrument having a light source, a computer processor and a light device controller and a plurality of light emitting devices in optical communication with the opto-electronic instrument where each of the light emitting devices has a plurality of states, and the opto-electronic instrument is adapted to produce a plurality of irradiance profile arrays for each of the plurality of states. Other embodiments of this aspect include corresponding computer systems, apparatus, and computer programs recorded on one or more computer storage devices, each configured to perform the actions of the methods.

Implementations may include one or more of the following features. The optical light delivery system may include a plurality of base cases representing the plurality of states of the plurality of light emitting devices. The optical light delivery system may include the computer processor including a neural network trained using at least the plurality of base cases and a tissue image pattern recognizer adapted to output a plurality of tissue image pixels and the neural network adapted to generate a plurality of optimized feature states using the plurality of tissue image pixels. The optical light delivery system may include the light device controller adapted to control the plurality of light emitting devices to produce a treatment irradiance profile using the plurality of optimized feature states. The plurality of light emitting devices is disposed at least partially within the light flap. The light flap is adapted to be applied to an area of interest of a patient to deliver the treatment irradiance profile to at least a portion of the area of interest. The optical light delivery system may include the treatment irradiance profile is delivered for a set period of time. The plurality of light emitting devices may include cylindrical light diffusers. The plurality of states is any of an off state, an on state, an intensity level and a wavelength. The optical light delivery system may include a fiber optic tether positioned between the plurality of light emitting devices and the opto-electronic instrument. Implementations of the described techniques may include hardware, a method or process, or computer software on a computer-accessible medium.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

Figure 1:
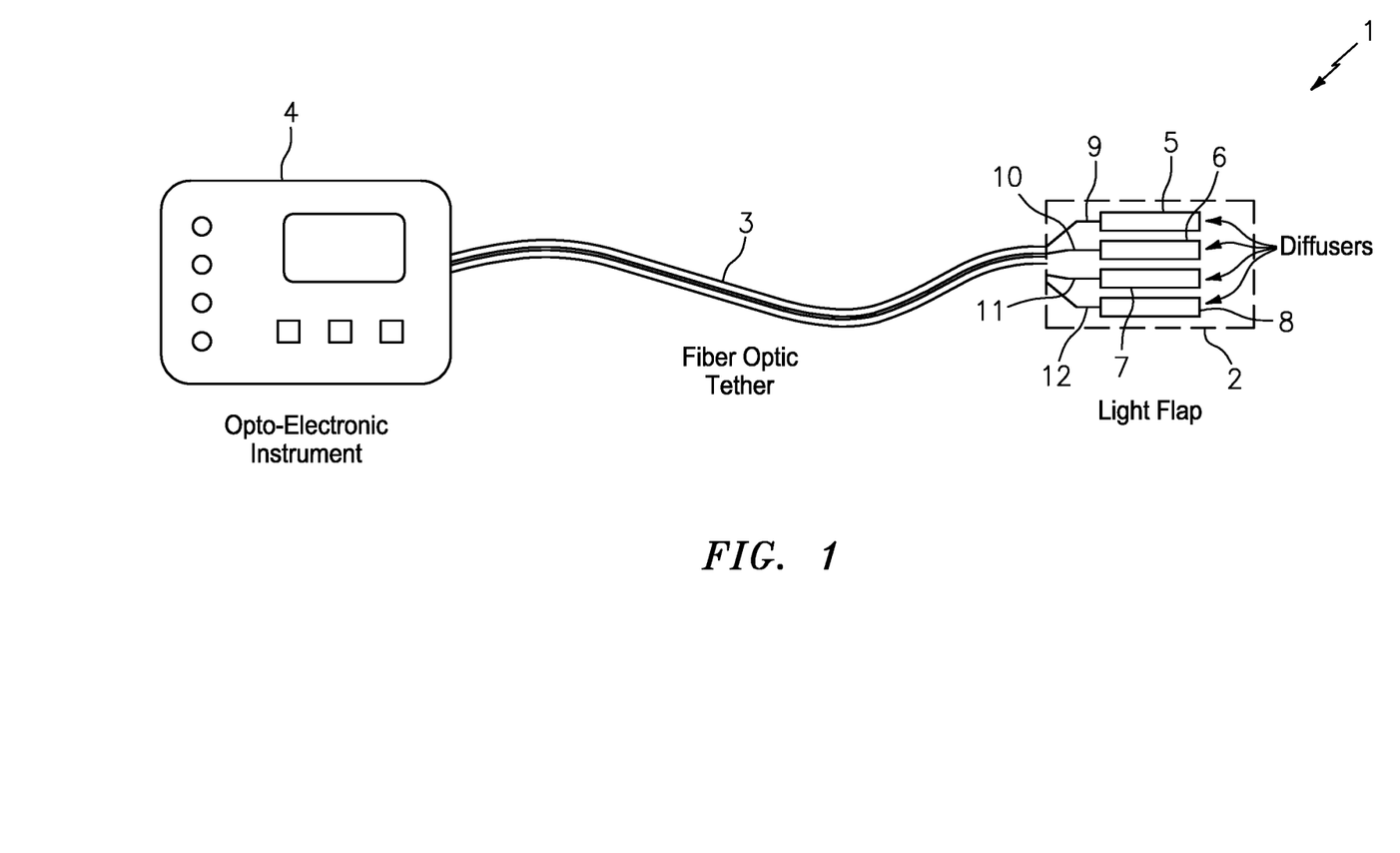
FIG. 1 is an illustration of a photodynamic therapy device in accordance with the present disclosure.

With reference to FIG. 1, there is shown an Optical Applicator Feature Optimizer (OAFO) 1 in accordance with certain embodiments of the current disclosure including light flap 2, fiber optic tether 3 and opto-electronic instrument (OEI) 4. Light flap 2 includes a plurality of light delivery devices such as optical diffusers 5, 6, 7, 8 positioned within the flap. In this particular embodiment optical diffusers 5, 6, 7, 8 are comprised of flexible cylindrical optical diffusers and are used to evenly diffuse light as will be described in detail herein after. Although this embodiment includes four optical diffusers 5, 6, 7, 8, other embodiments are contemplated having more than four and fewer than four. It should be noted that optical diffusers 5, 6, 7, 8 cause light to spread evenly across a surface and are also known as light diffusers in many prior art illumination applications. Optical diffusers 5, 6, 7, 8 can comprise any known type of optical diffuser such as cylindrical light diffusers provided by Pioneer Optics as disclosed at https://www.pioneeroptics.com/Diffusers.html. Light flap 2 can comprise and suitable material having the flexibility to conform to a tissue surface and having the light transmissibility qualities to allow light emanating from optical diffusers 5, 6, 7, 8. Fiber optic tether 3 includes a plurality of optical fibers 9, 10, 11, 12 routed therethrough and respectively optically couple to optical diffusers 5, 6, 7, 8 and in optical communication with OEI 4. OEI 4 includes user input controls, display 13 and includes a processor, software storage capability and wireless communications devices such as Bluetooth and WiFi. The software can include neural network capability and pattern recognition capabilities as will be described in more detail herein after.

Figure 2:
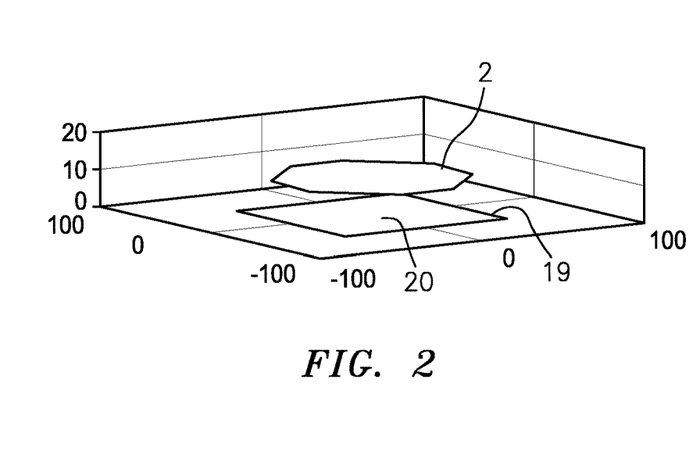
FIG. 2 is graphical representation of a base case light intensity profile in accordance with the present disclosure.
Figure 3:
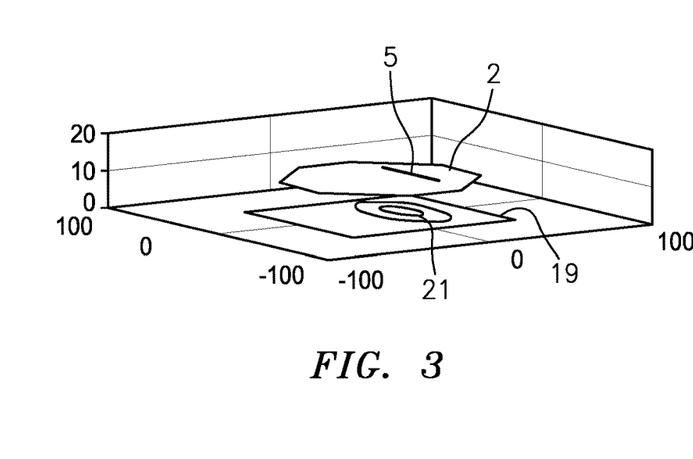
FIG. 3 is graphical representation of a base case light intensity profile in accordance with the present disclosure.
Figure 4:
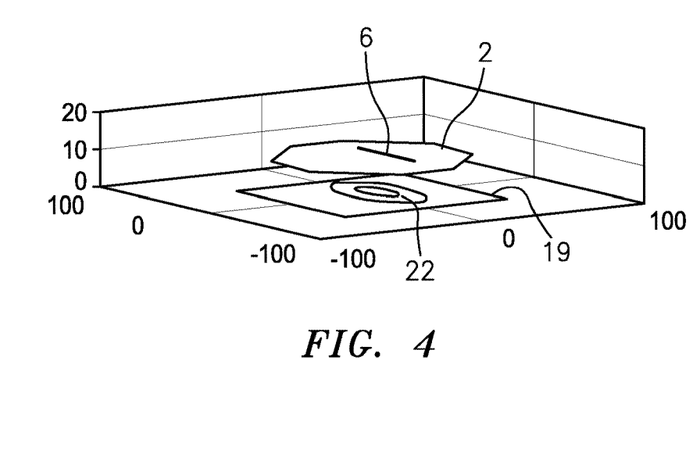
FIG. 4 is graphical representation of a base case light intensity profile in accordance with the present disclosure.
Figure 5:
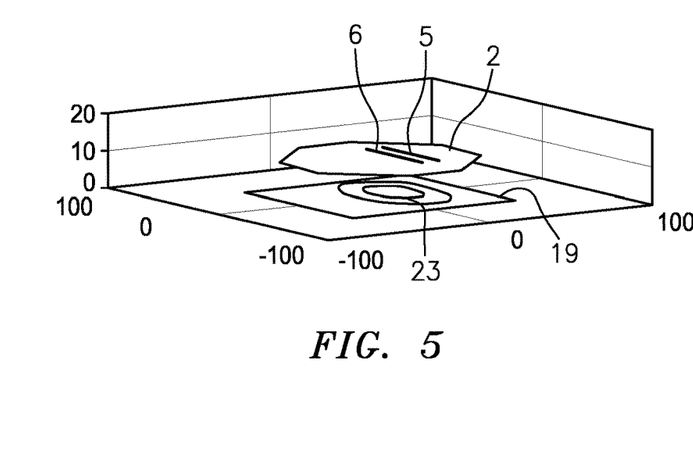
FIG. 5 is graphical representation of a base case light intensity profile in accordance with the present disclosure.
Figure 6:
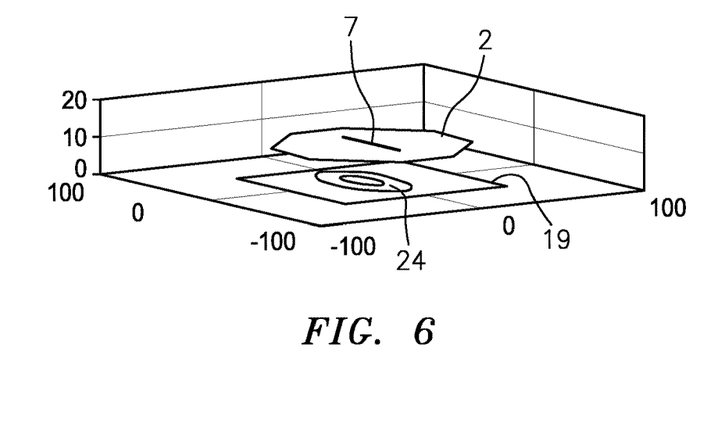
FIG. 6 is graphical representation of a base case light intensity profile in accordance with the present disclosure.
Figure 7:
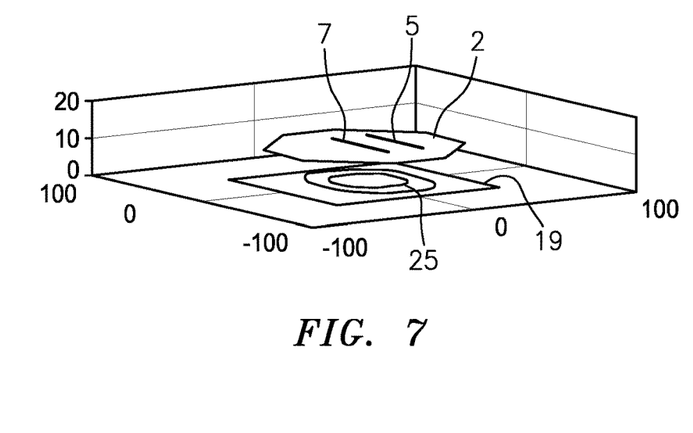
FIG. 7 is graphical representation of a base case light intensity profile in accordance with the present disclosure.
Figure 8:
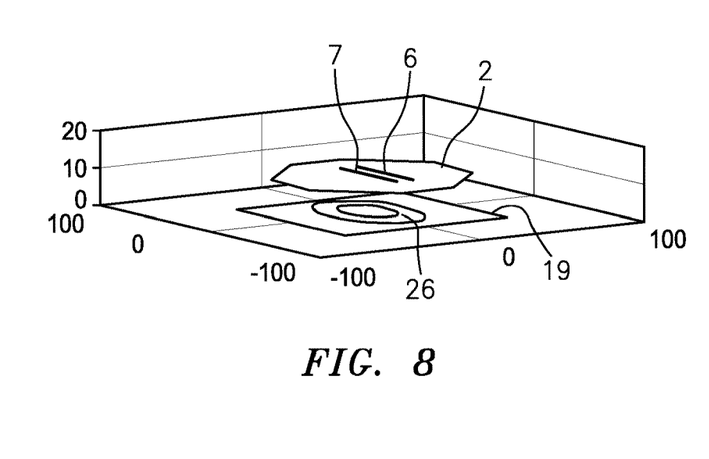
FIG. 8 is graphical representation of a base case light intensity profile in accordance with the present disclosure.
Figure 9:
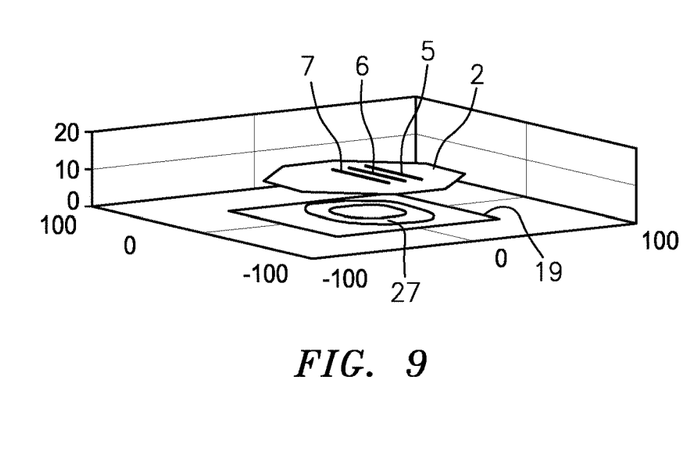
FIG. 9 is graphical representation of a base case light intensity profile in accordance with the present disclosure.
Figure 10:
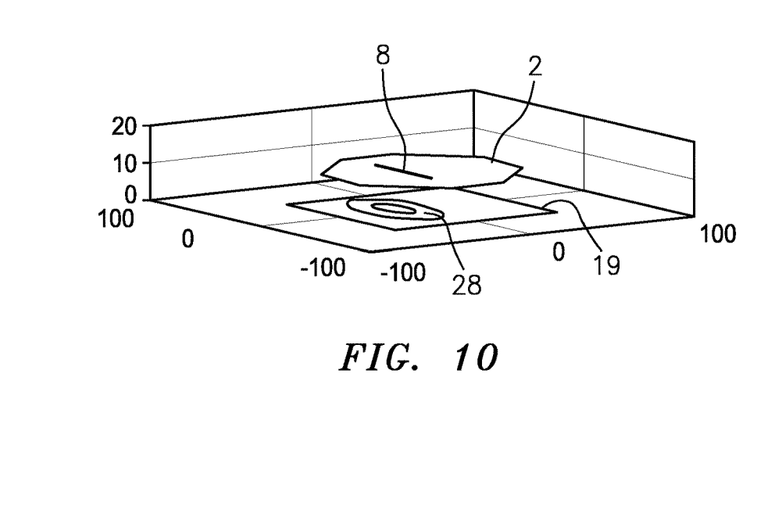
FIG. 10 is graphical representation of a base case light intensity profile in accordance with the present disclosure.
Figure 11:
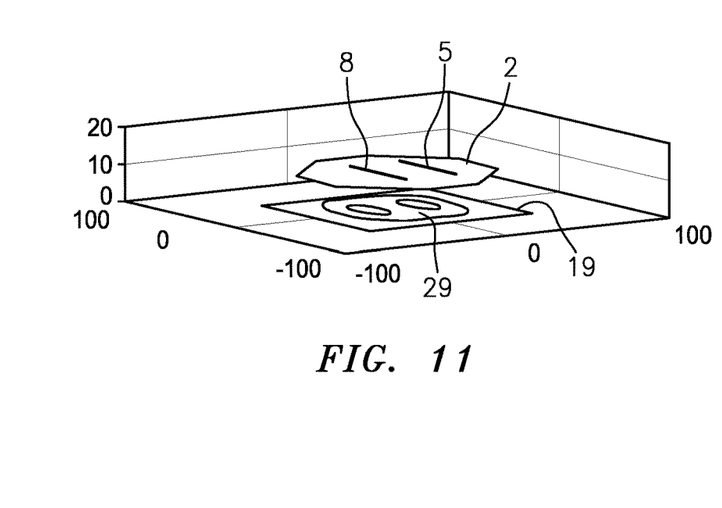
FIG. 11 is graphical representation of a base case light intensity profile in accordance with the present disclosure.
Figure 12:
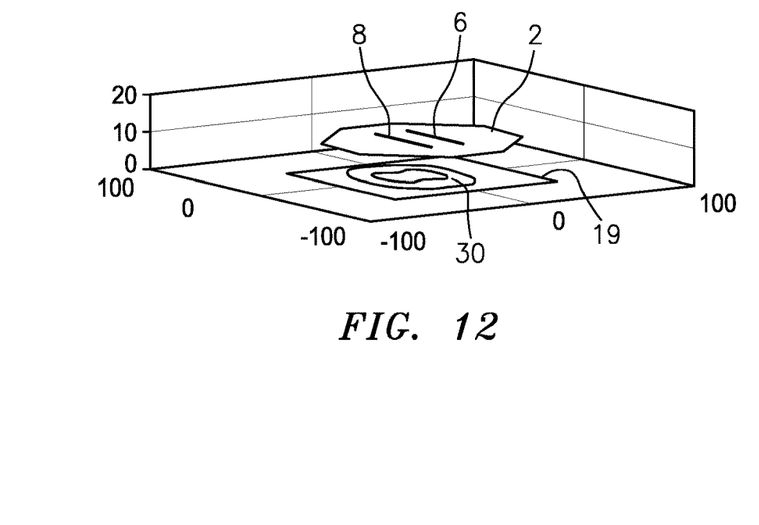
FIG. 12 is graphical representation of a base case light intensity profile in accordance with the present disclosure.
Figure 13:
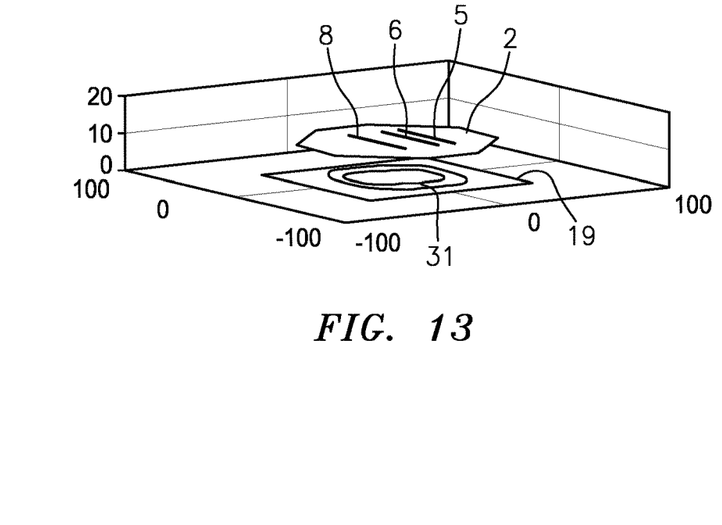
FIG. 13 is graphical representation of a base case light intensity profile in accordance with the present disclosure.
Figure 14:
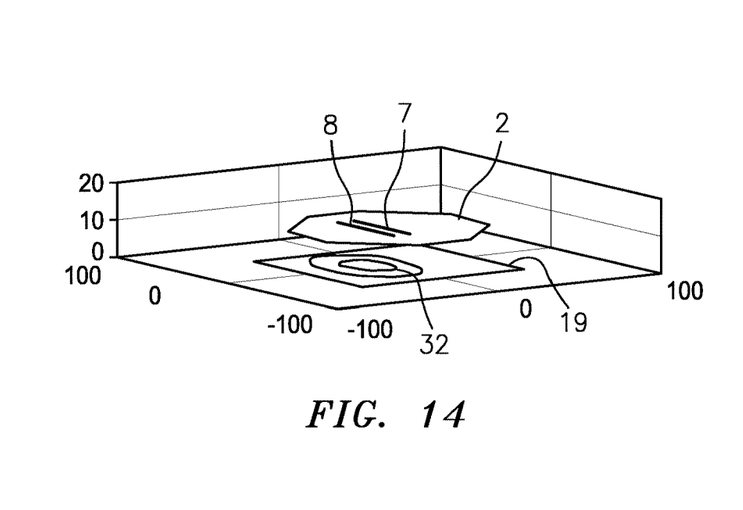
FIG. 14 is graphical representation of a base case light intensity profile in accordance with the present disclosure.
Figure 15:
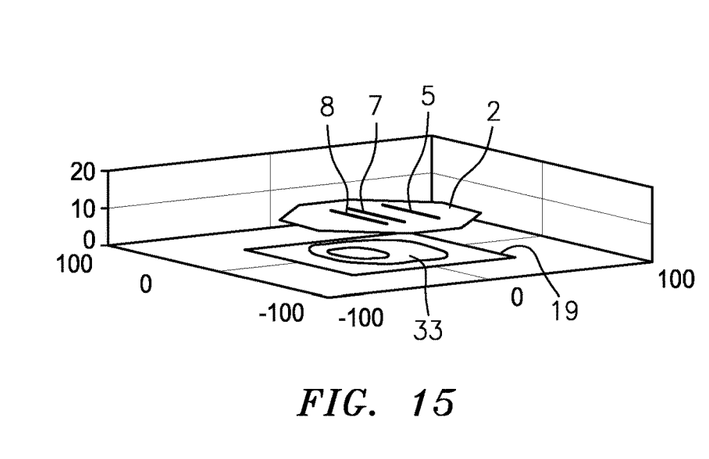
FIG. 15 is graphical representation of a base case light intensity profile in accordance with the present disclosure.
Figure 16:
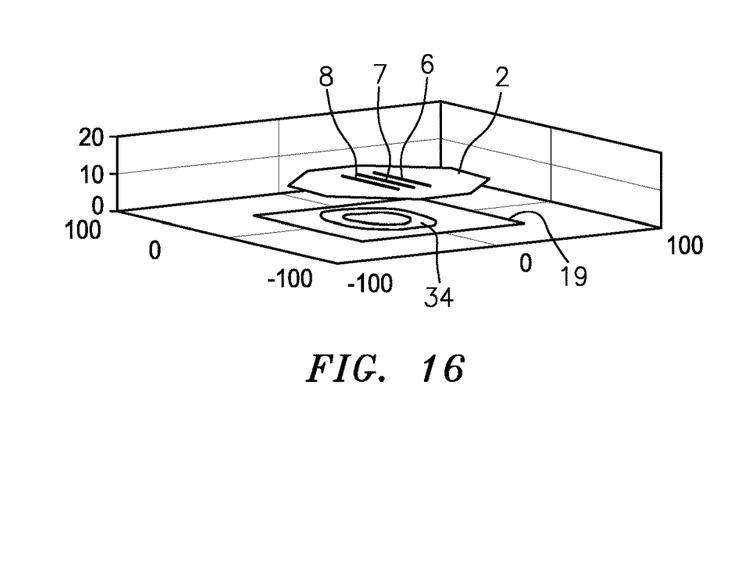
FIG. 16 is graphical representation of a base case light intensity profile in accordance with the present disclosure.
Figure 17:
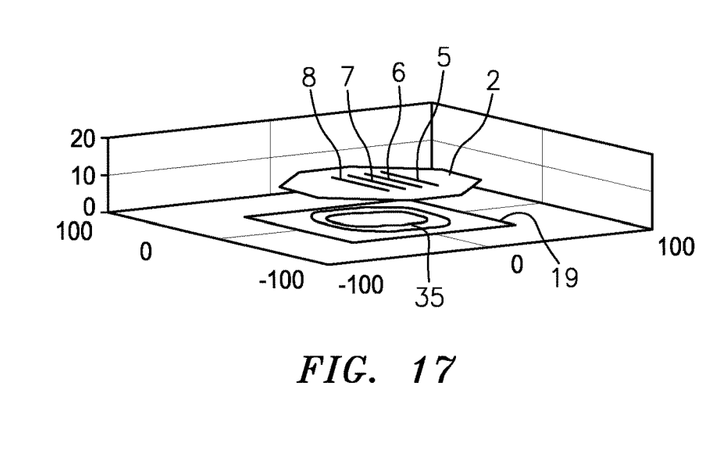
FIG. 17 is graphical representation of a base case light intensity profile in accordance with the present disclosure.

OEI 4 further includes at least one light source and a controller adapted to control a state of light output to the plurality of optical fibers 9, 10, 11, 12 wherein the state can at least include light on, light off, intensity and wavelength, among others. The OAFO 1 of the present disclosure can provide precise control of a delivered irradiance profile array depending, in part, on the number of light delivery devices and the number of states that OEI 4 can control. For example, the control of a delivered irradiance profile array of OAFO 1 of FIG. 1, when considering the four optical diffusers 5, 6, 7, 8 and the two states of light output of (1) light on and (2) light off, is $2^4$ or 16 distinct irradiance profile arrays. The 16 distinct irradiance profile arrays are referred to herein as base cases. The base cases in this example can best be seen with reference to FIGS. 2-17, where in FIG. 2 all four optical diffusers 5, 6, 7, 8 within flap 2 are in the off state and no light is projected onto surface 19 producing a dark irradiance profile array 20. In FIG. 3, optical diffusers 6, 7, 8 are in the off state and optical diffuser 5 is in the on state producing irradiance profile array 21. In FIG. 4, optical diffusers 5, 7, 8 are in the off state and optical diffuser 6 is in the on state producing irradiance profile array 22. In FIG. 5, optical diffusers 7, 8 are in the off state and optical diffusers 5, 6 are in the on state producing irradiance profile array 23. In FIG. 6, optical diffusers 5, 6, 8 are in the off state and optical diffuser 7 is in the on state producing irradiance profile array 24. In FIG. 7, optical diffusers 6, 8 are in the off state and optical diffusers 5, 7 are in the on state producing irradiance profile array 25. In FIG. 8, optical diffusers 5, 8 are in the off state and optical diffusers 6, 7 are in the on state producing irradiance profile array 26. In FIG. 9, optical diffuser 8 is in the off state and optical diffusers 5, 6, 7 are in the on state producing irradiance profile array 28. In FIG. 10, optical diffusers 5, 6, 7 are in the off state and optical diffuser 8 is in the on state producing irradiance profile array 28. In FIG. 11, optical diffusers 6, 7 are in the off state and optical diffusers 5, 8 are in the on state producing irradiance profile array 28. In FIG. 12, optical diffusers 5, 7 are in the off state and optical diffusers 6, 8 are in the on state producing irradiance profile array 30. In FIG. 13, optical diffuser 7 is in the off state and optical diffusers 5, 6, 8 are in the on state producing irradiance profile array 31. In FIG. 14, optical diffusers 5, 6 are in the off state and optical diffusers 7, 8 are in the on state producing irradiance profile array 32. In FIG. 15, optical diffuser 6 is in the off state and optical diffusers 5, 7, 8 are in the on state producing irradiance profile array 33. In FIG. 16, optical diffuser 5 is in the off state and optical diffusers 6, 7, 8 are in the on state producing irradiance profile array 34. Finally, in FIG. 17, all of the plurality of optical diffusers 5, 6, 7, 8 are in the on state producing irradiance profile array 35. The irradiance profile arrays 20-35 can be generated using, among other things, a computer driven profile calculator using the specific optical properties of the light source of OEI 4, optical fibers 9-12, optical diffusers 5-8 and the geometrical position and properties of the optical diffusers and flap 2 wherein each of the irradiance profile arrays comprises a light image data file for each of the states of the light emitting devices 5-8. For example, OAFO 1 can be modeled using MATLAB® to produce the light image data files for the irradiance profile arrays for each of the base cases.

In the example disclosed above, the light image data files for irradiance profile arrays 20-35 can be sub-divided into pixels. For instance, a given irradiance profile array can include an array of pixels having a size of 101×101 pixels for a total of 10,201 pixels for each of the base cases described with reference to FIGS. 2-17. Each pixel includes a portion of the light image data representing a respective portion of each of the plurality of irradiance profile arrays for each of the base cases wherein each of the pixels is assigned a specific intensity level. In accordance with the present disclosure, a set of training cases is developed using the aforementioned bases cases. In some embodiments, the light image data files for irradiance profile arrays 20-35 from the base cases can be altered using computer modeling software such as MATLAB® to produce a training set of image data files representing irradiance profile arrays. The training cases can be altered using any number of array modifiers such as performing geometric perturbations, normalizing to a grayscale value, introducing a jitter, among others. In a particular embodiment, a semi-random array modifier is used for each one of the bases cases to produce a plurality of training cases wherein the training cases can be in the hundreds of sets of image data files representing irradiance profile arrays. The base cases and the training cases can then be combined into a training set and can be used to train the neural network using machine learning techniques. In the training of the neural network, and as will be described in more detail herein below, the resulting irradiance profile array for each of the training cases is calculated and provides as a result to the neural network such that the neural network "learns" what the statistically appropriate answer is for a given input.

Figure 18:
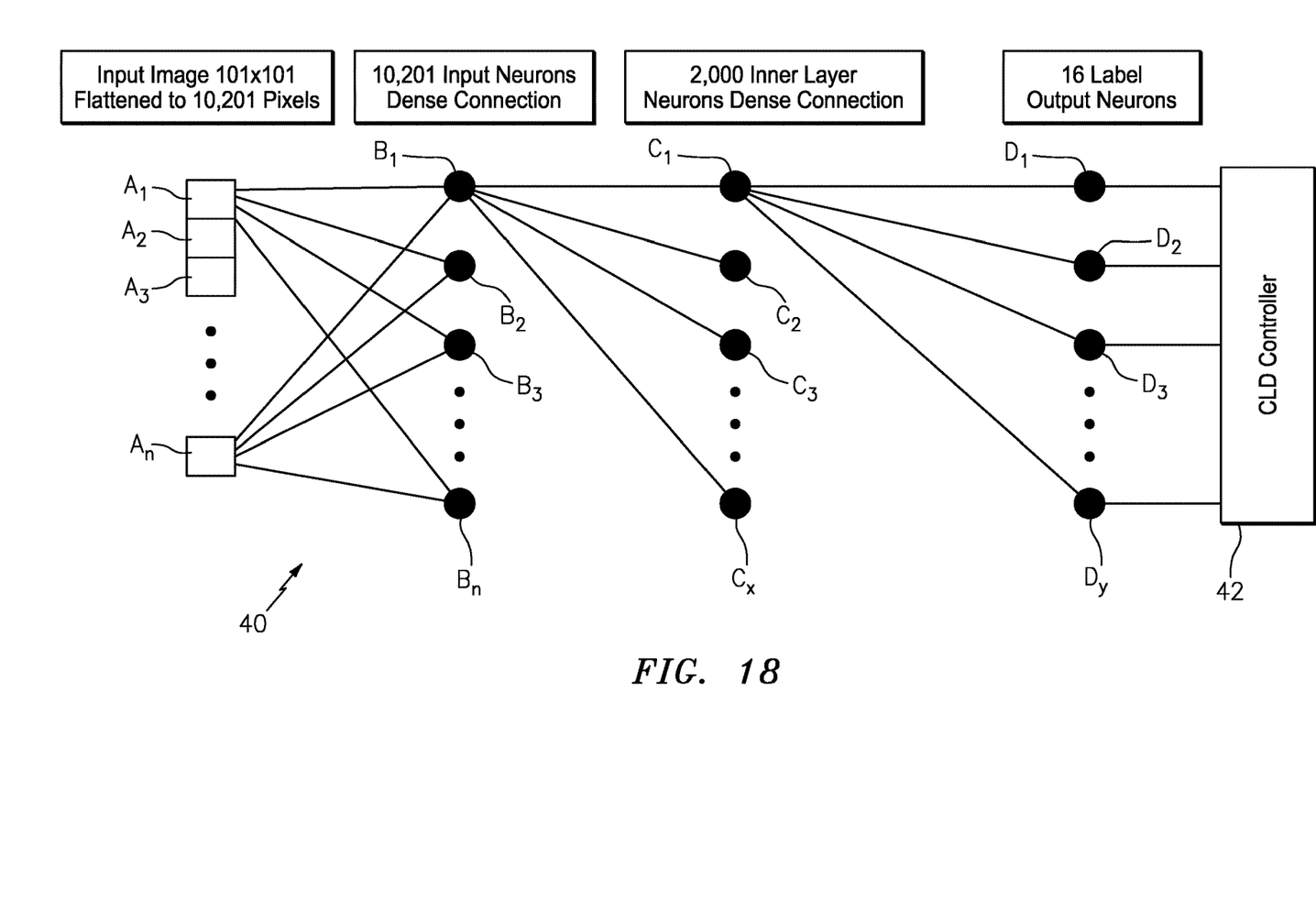
FIG. 18 is schematic representation of a computer system in accordance with the present disclosure.

As will be disclosed in detail herein below, OAFO 1 of FIG. 1 can use a trained neural network to produce a specific light irradiance pattern to match a digital image of tissue for treating the tissue using I-PDT techniques. Using the example described herein above, the plurality of irradiance profile arrays for the training set each include an array of pixels having a size of 101×101 pixels. With reference to FIG. 18, using computer system 40, the 101×101 array of pixels for each array of the training set is flattened to a 1×10,201 input array having $A_1$-$A_n$ pixels (where n is 10,201 in this particular example). Computer system 40 can comprise any known computer system, computer processor, various types of memory and peripheral devices. As described herein above, each of the pixels is assigned its corresponding intensity value and the input array of $A_1$-$A_n$ pixels are input into the computer system as the input neurons $B_1$-$B_n$ (where n is 10,201 in this particular example) in the input layer of the neural network. The neural network model can reside as software on computer system 40, it can be cloud based software or it can reside on a network. In turn, the input neurons are connected to, and provide input to, at least one inner layer of neurons $C_1$-$C_x$ (where x is 2000 in this particular example). The inner layer of neurons $C_1$-$C_x$ uses a set of shared weights and biases to detect features in the input neurons, say an edge of an intensity profile, at different positions within the input neurons. The machine learning process includes a set of output neurons $D_1$-$D_y$ for each of the plurality of irradiance profile arrays for the training set. As disclosed herein above, these output neurons $D_1$-$D_y$ for each of the plurality of irradiance profile arrays for the training set are calculated and input to the neural network for training the model. Once the training sets have been run through the neural network of computer system 40 and comprises the trained neural network model. In the case of the output neurons $D_1$-$D_y$, y is 16 and it represents the control parameters of the four optical diffusers 5, 6, 7, 8 (FIG. 1) and the two states of light output. The output neurons $D_1$-$D_y$ are used as input into light device controller 42 of OEI 4 to produce a desired therapeutic irradiance profile as will be described more fully herein below.

Similar to that disclosed herein above related to producing the training cases, a set of test cases can be generated from the base cases. The light image data files for irradiance profile arrays 20-35 (FIGS. 2-17) from the base cases are similarly altered using computer modeling software to produce the test set of image data files representing irradiance profile arrays. In a particular embodiment, a semi-random array modifier is used for each one of the bases cases to produce a plurality of test cases wherein the test cases can be in the tens of sets of image data files representing irradiance profile arrays. The test cases form a test set of irradiance profile arrays and the test set is used as input to the computer system 40. Using the test set of irradiance profile arrays the trained neural network model produces a set of optimized test output neurons $D_1$-$D_y$. The set of optimized test output neurons $D_1$-$D_y$ comprise a set of optimized feature states for each of the light emitting devices 5-8 statistically selected from the 16 base cases of FIGS. 2-17. In the example here, the states are either on or off for each of the four light emitting devices 5-8. The optimized feature states for the test output neurons are compared to that of the calculated states for the training output neurons. If the two sets closely match, the input of image data into the trained neural network will produce an accurate output file for producing a desired light intensity profile as will be described herein after. As part of the present disclosure the trained neural network model is either hosted on, or otherwise accessed by, OEI 4 (FIG. 1).

Figure 19:
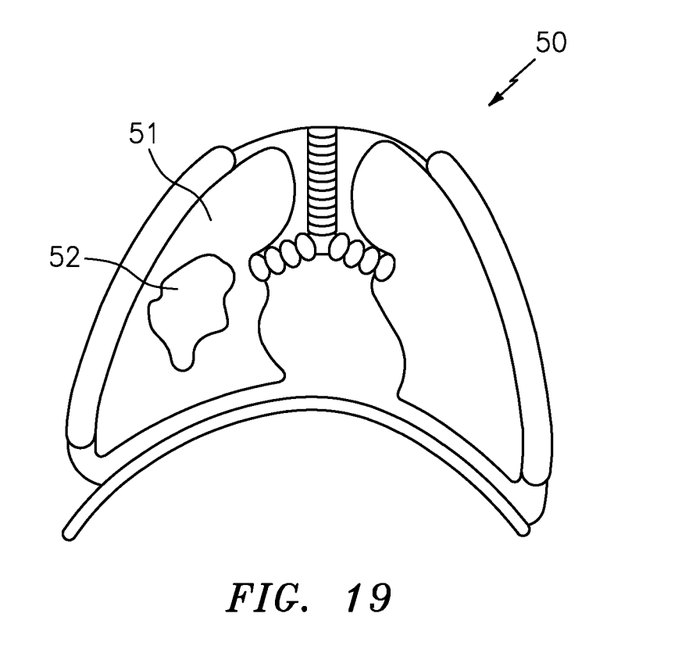
FIG. 19 is an illustration of a tissue image in accordance with the present disclosure.

Now referring to FIG. 19, there is shown an example of an image 50 of tissue 51 including a tumor 52. Image 50 can be any type of diagnostic image such as x-ray, Computed Tomography (CT), Magnetic Resonance Imaging (MRI) or other known medical imaging technologies. Many of the known medical imaging technologies are digital images and others can be digitally scanned using known techniques. It is known in the prior art that neural networks can be used to identify areas of interest of tissue 51 having high probabilities of the presence of a tumor 52 using, for example, a tissue image pattern recognizer. The output of such neural networks can include a digital data file of the shape and position of tumor 52 in the form of a two-dimensional array of grey level pixel values. Using computer system 40 of FIG. 18, the processor of OEI 4 (FIG. 1) for example, the two-dimensional grey level pixel values are flattened into a one-dimensional array. The one-dimensional array is processed to extract optimized feature values of the area of interest, namely of the tumor 52. The optimized feature value of the area of interest are subdivided into a plurality of tissue image pixels (or normalized) into a 1×n array. The 1×n array of is used as input $A_1$-$A_n$ of the trained neural network disclosed herein above. The trained neural network produces a statistically optimized set of therapeutic output neurons $D_1$-$D_y$ representing a plurality of optimized feature states of the four optical diffusers 5, 6, 7, 8 (FIG. 1). The optimized feature states determined by output neurons $D_1$-$D_y$ are used as input into light device controller 42 of OEI 4 to produce a desired therapeutic irradiance profile that closely matches the shape and location of the area of interest of tumor 52.

Figure 20:
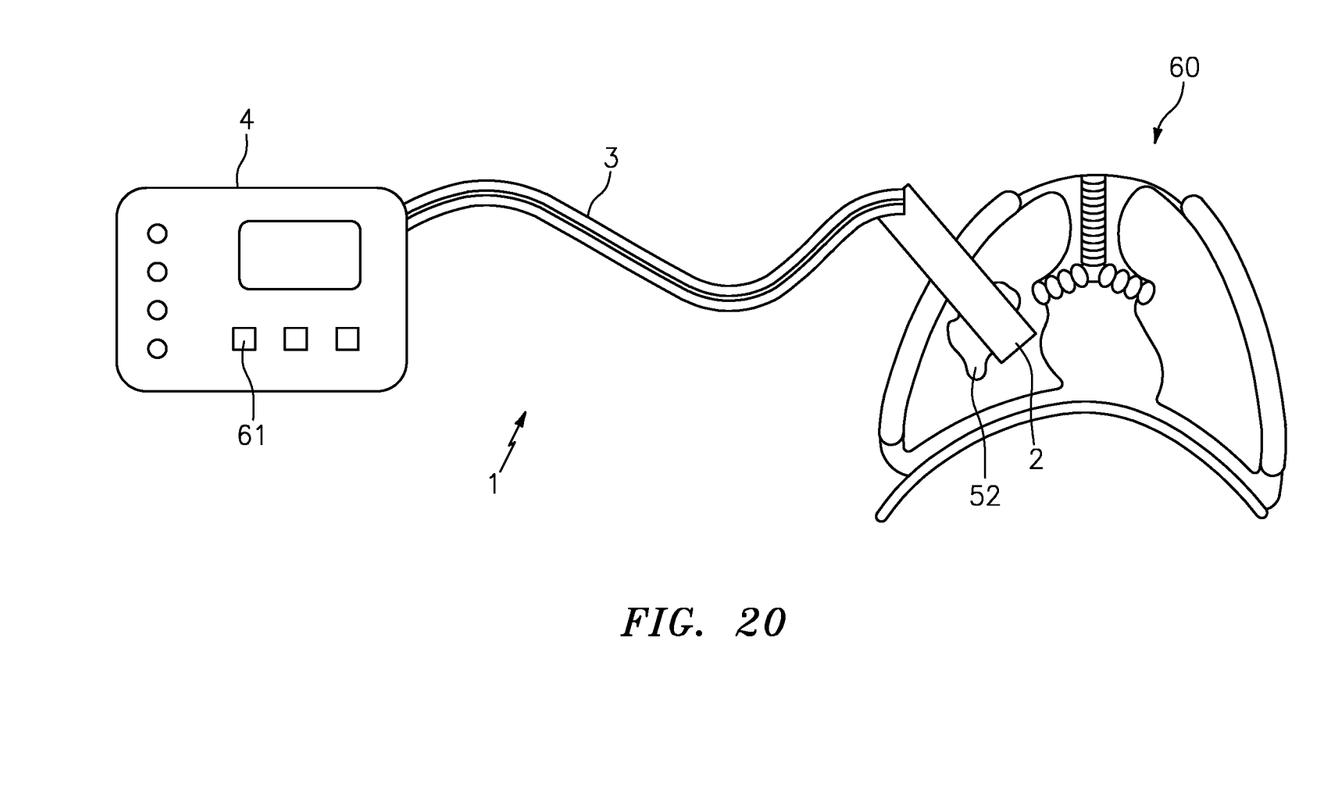
FIG. 20 is an illustration of the use of a photodynamic therapy device in accordance with the present disclosure.

The operation of an embodiment of OAFO 1 is best described by referring to FIG. 20. The OAFO 1 can be, for example, the embodiment described herein above wherein the OAFO includes OEI 4, optical tether 3 and light flap 4 having four optical diffusers 5-8 disposed therein. OAFO 1 further includes the trained neural network described herein above to determine the plurality of irradiance profile arrays 20-35 (FIGS. 2-17). A user inputs digital image 50 of tumor 52 (FIG. 19) to the processor of OAFO 4 as input into the trained neural network. Using the method described herein with respect to FIG. 18, the neural network determines the position of the tumor 52, or excised tumor area, within patient 60, shown by way of example the tumor is positioned within a lung of the patient. The user, typically a surgeon or skilled assistant, positions light flap 2 over tumor 52 in accordance with the position information obtained from image 50. The user then selects button 61 on OAFO 4 and the processor within the OAFO which uses the plurality of optimized feature states determined by the trained neural network to command light device controller 42 produce an optimized a treatment irradiance profile that most closely matches tumor 52 from all of the state producing irradiance profile arrays 20-35. It should be apparent by those skilled in the art that, by applying the optimized a treatment irradiance profile via a single operation of depressing button 61, a precise interoperative PDT light therapy, both in terms of position and dosimetry pattern, can be administered to patient 60 in a real time automated fashion. Once treatment has begun as described, the processor of OAFO 4 control optical diffusers 5-6, individually or collectively, for a predetermined amount of time to optimize the PDT in accordance with predetermined exposure times. In circumstances where light flap 2 is larger than tumor 52, the treatment irradiance profile will only include those number of light diffusers necessary to produce the optimized treatment pattern. In circumstances where light flap 2 is smaller than tumor 52, OAFO 1 will output more than one optimized treatment irradiance profiles from the of optimized feature states. The user will position the light flap 2 sequentially in accordance with each of the more than one optimized treatment irradiance profiles and perform the treatment procedure at each such location as described herein above.

Although disclosed herein above with respect to an embodiment of OAFO 1 having a light flap 4 having four optical diffusers 5-8 disposed therein and each of the light diffusers having only two states, it is within the scope of the present disclosure that the OAFO can include an enhanced OAFO having other features and parameters to produce optimized treatment irradiance profiles with greater resolution in terms of spatial resolution, temporal resolution and dosimetry resolution. For example, in embodiments that include six light diffusers (instead of four), which can be positioned adjacent to one another to form a 1×6 array or end-to-end to form a 2×3 array or other pattern, and each of the six light diffusers have two states (on and off) the plurality of states grows from 16 bases cases to $2^6$ or 64 base cases each having a distinct irradiance profile array. Such an embodiment would provide greater spatial resolution to determine an optimized treatment irradiance profile from a greater number of optimized feature states that more closely matches the location, shape and size of tumor 52. In addition, processor of OAFO 4 can control the optical diffusers, individually or collectively, for a predetermined amount of time to optimize the PDT in accordance with predetermined exposure times which provides for greater dosimetry resolution and temporal control. In other embodiments of OAFO 1 (FIG. 1) of the present disclosure, the light source of the OAFO can include features to vary the intensity of the light transmitted through fiber optic tether 3 to the four optical diffusers 5-8 to increase the number of optimized feature states and produce an optimized treatment irradiance profile having greater resolution. For instance, in an embodiment where the light source of OAFO 1 had four states, namely off, low, medium and high, delivered to each of the four light diffusers 5-8 the plurality of states grows from 16 bases cases to $4^4$ or 256 base cases each having a distinct irradiance profile array. Such an embodiment would provide greater dosimetry resolution to determine an optimized treatment irradiance profile from a greater number of optimized feature states for a predetermined dosimetry amount of time to optimize the PDT in accordance with predetermined dosimetry plan. In these, and other, alternative embodiments of OAFO's, each of the base cases are modeled to produce irradiance profile arrays, training cases are formed and the neural network is trained as described herein before. The image 50 of the tumor 52 is input into the neural network and a plurality of optimized feature states are produced with the trained neural network and an optimized treatment irradiance profile produced therefrom. The optimized treatment irradiance profile is used to treat a patient in the manner described with reference to FIG. 20 herein above.

While the foregoing is directed to embodiments of the present invention, other and further embodiments of the invention may be devised without departing from the basic scope thereof, and the scope thereof is determined by the claims that follow.

What is claimed is:

1. A method for controlling an optical light delivery system, the method comprising:
providing a plurality of light emitting devices wherein each of the light emitting devices has a plurality of states;
producing a plurality of irradiance profile arrays for each of the plurality of states of the plurality of light emitting devices;
subdividing each of the plurality of irradiance profile arrays into a plurality of pixels, each pixel comprising a portion of each of the plurality of irradiance profile arrays;
determining a specific intensity level for each of the pixels;
assigning a value to each of the pixels in accordance with the specific intensity level; and
generating a plurality of base cases representing the plurality of states of the plurality of light emitting devices.

2. The method of claim 1, further comprising:
generating a plurality of training cases, wherein at least one training case is generated by performing at least one operation on at least one base case, the at least one operation selected from the group consisting of:
performing a semi-random array modifier to the base case;
performing geometric perturbations to the base case;
normalizing a grayscale value of the base case; and
introducing a jitter into the base case.

3. The method of claim 2, further comprising:
creating a neural network model;
training the neural network model using at least the plurality of base cases and
the plurality of training cases; and
producing a trained neural network.

4. The method of claim 3, further comprising:
receiving tissue image data representing an organ;
identifying an area of interest from the tissue image data;
subdividing the area of interest into a plurality of tissue image pixels, each tissue image pixel comprising a portion of the area of interest representing a respective portion of the organ;
inputting the plurality of tissue image pixels into the trained neural network;
determining a plurality of optimized feature states; and
outputting the plurality of optimized feature states.

5. The method of claim 4, further comprising:
controlling the plurality of light emitting devices using the plurality of optimized feature states; and
producing a treatment irradiance profile closely matching at least a portion of the area of interest.

6. The method of claim 4, wherein the area of interest comprises a tumor.

7. The method of claim 5, further comprising:
positioning the plurality of light emitting devices proximate at least a portion of the area of interest; and
delivering the treatment irradiance profile to the area of interest.

8. The method of claim 7, wherein the treatment irradiance profile is delivered to the area of interest for a set period of time.

9. The method of claim 1, wherein the plurality of states is any of an off state, an on state, an intensity level and a wavelength.

* * * * *